(12) United States Patent
Smith et al.

(10) Patent No.: US 7,648,488 B2
(45) Date of Patent: Jan. 19, 2010

(54) WOUND CARE SYSTEM

(75) Inventors: Joshua David Smith, Nashville, TN (US); David Myron Smith, Burns, TN (US); Thomas G. Andrews, Nashville, TN (US); Jack Fisher, Nashville, TN (US); David P. Bohman, Nashville, TN (US); Robert Stephen Porter, Brentwood, TN (US)

(73) Assignee: Pioneer Technology, LLC, Nashville, TN (US)

( * ) Notice: Subject to any disclaimer, the term of this patent is extended or adjusted under 35 U.S.C. 154(b) by 0 days.

(21) Appl. No.: 11/602,653

(22) Filed: Nov. 21, 2006

(65) Prior Publication Data

US 2007/0118096 A1    May 24, 2007

Related U.S. Application Data

(60) Provisional application No. 60/738,690, filed on Nov. 21, 2005.

(51) Int. Cl.
   *A61M 1/00*    (2006.01)
(52) U.S. Cl. .................... 604/313; 604/46; 604/304; 604/305; 604/308; 604/315
(58) Field of Classification Search .................. 604/313, 604/454, 308, 46, 315, 305, 304
   See application file for complete search history.

(56) References Cited

U.S. PATENT DOCUMENTS

| | | | |
|---|---|---|---|
| 4,979,944 A * | 12/1990 | Luzsicza | 604/118 |
| 5,009,635 A * | 4/1991 | Scarberry | 604/27 |
| 5,636,643 A | 6/1997 | Argenta et al. | |
| 5,645,081 A | 7/1997 | Argenta et al. | |
| 6,071,267 A | 6/2000 | Zamierowski | |
| 6,142,982 A * | 11/2000 | Hunt et al. | 604/313 |
| 6,458,109 B1 | 10/2002 | Henley et al. | |
| 6,755,807 B2 | 6/2004 | Risk, Jr. et al. | |
| 6,767,334 B1 | 7/2004 | Randolph | |
| 6,800,074 B2 | 10/2004 | Henley et al. | |

(Continued)

FOREIGN PATENT DOCUMENTS

WO    WO 96/33767    10/1996

(Continued)

OTHER PUBLICATIONS

Madalene C.Y. Heng, MB, FRACP, FACD, Topical Hyperbaric Therapy for Problem Skin Wounds,The Journal of Dermatologic Surgery and Oncology, Aug. 1993, 784-792, vol. 19, Elsevier Science Publishing Co., Inc., New York, New York USA.

(Continued)

*Primary Examiner*—Michele Kidwell
*Assistant Examiner*—Ilya Y Treyger
(74) *Attorney, Agent, or Firm*—Renner Otto Boisselle & Sklar

(57) ABSTRACT

Disclosed is an apparatus for the treatment of a wound on a patient. The apparatus is capable of administering localized negative pressure therapy to the wound using a negative pressure source and a drain line for removing exudate from the wound. The apparatus is also capable of administering localized hyperbaric fluid therapy to the wound using a fluid source and a supply line for supplying fluid to the wound.

10 Claims, 9 Drawing Sheets

U.S. PATENT DOCUMENTS

| | | | |
|---|---|---|---|
| 6,951,553 B2 * | 10/2005 | Bubb et al. | 604/327 |
| 6,979,324 B2 | 12/2005 | Bybordi et al. | |
| 7,276,051 B1 | 10/2007 | Henley et al. | |
| 2002/0120185 A1 | 8/2002 | Johnson | |
| 2002/0183702 A1 | 12/2002 | Henley et al. | |
| 2003/0212357 A1 | 11/2003 | Pace | |

FOREIGN PATENT DOCUMENTS

| WO | WO 00/07653 | 2/2000 |
|---|---|---|
| WO | WO 03/092620 | 11/2003 |
| WO | WO 2005/105174 | 11/2005 |

OTHER PUBLICATIONS

Theodor Kaufman, M.D., et al., The Microclimate Chamber: The Effect of Continuous Topical Administration of 96% Oxygen and 75% Relative Humidity on the Healing Rate of Experimental Deep Burns, The Journal of Trauma, Sep. 1983, 806-815, vol. 23, Williams & Wilkins, Baltimore, MD USA.

Frank E. Johnson, M.D., F.A.C.S., "An Improved Technique for Skin Graft Placement Using a Suction Drain", Surgery Gynecology & Obstetrics, Dec. 1984, 585-586, vol. 159, No. 6, St. Louis, MS USA.

Pal Svedman, "A Dressing Allowing Continuous Treatment of a Biosurface", IRCS Medical Science: Biomedical Technology; Clinical Medicine; Surgery and Transplantation, Mar. 27, 1979, One page, Department of Plastic Surgery, Malmo General Hospital, Malmo, Sweden.

Diane M. Cooper, PhD. RN, "The Physiology of Wound Healing: An Overview," Chronic Wound Care: A Clinical Source Book for HealthCare Professionals, 1990, Chapter 1(1-11), Health Management Publications, Inc., King of Prussia, PA USA.

Keith G. Harding, MB, ChB, MRCGP, "Wound Care: Putting Theory Into Clinical Practice", Chronic Wound Care: A Clinical Source Book for HealthCare Professionals, 1990, Chapter 3 (19-30), Health Management Publications, Inc., King of Prussia, PA USA.

TD Turner, OBE, MPharm, FRPharms, FLS, MCPP, "The Development of Wound Management Products", Chronic Wound Care: A Clinical Source Book for HealthCare Professionals, 1990, Chapter 4 (31-46), Health Management Publications, Inc., King of Prussia, PA USA.

Katherine F. Jeter, EdD, ET, "Managing Draining Wounds and Fistulae: New and Established Methods", Chronic Wound Care: A Clinical Source Book for HealthCare Professionals, 1990, Chapter 27 (240-246), Health Management Publications, Inc., King of Prussia, PA USA.

Linda K. Klein, BSN, MS, CETN, "Topical Treatment for Chronic Wounds: An Overview", Chronic Wound Care: A Clinical Source Book for HealthCare Professionals, 1990, Chapter 31 (263-265), Health Management Publications, Inc., King of Prussia, PA USA.

Oscar Alvarez, MD, PhD, "Principles of Moist Wound Healing: Indications for Chronic Wounds", Chronic Wound Care: A Clinical Source Book for HealthCare Professionals, 1990, Chapter 32 (266-281), Health Management Publications, Inc., King of Prussia, PA USA.

George T. Rodeheaver, PhD., "Controversies in Topical Wound Management: Wound Cleansing And Wound Disinfection", Chronic Wound Care: A Clinical Source Book for HealthCare Professionals, 1990, Chapter 33 (282-289), Health Management Publications, Inc., King of Prussia, PA USA.

S. Randolph May, PhD, "An Algorithm For Wound Management With Natural and Synthethic Dressings", Chronic Wound Care: A Clinical Source Book for HealthCare Professionals, 1990, Chapter 36 (301-308), Health Management Publications, Inc., King of Prussia, PA USA.

Cecilia R. Rund, RN, CETN, "Alternative Treatments—Alternative Settings", Chronic Wound Care: A Clinical Source Book for HealthCare Professionals, 1990, Chapter 37 (309-317), Health Management Publications, Inc., King of Prussia, PA USA.

Keith Van Meter, MD, FACEP, "Baromedicine in Chronic Wound Care", Chronic Wound Care: A Clinical Source Book for HealthCare Professionals, 1990, Chapter 42 (391-409), Health Management Publications, Inc., King of Prussia, PA USA.

Greg Skover, PhD, "New Technologies: An Overview", Chronic Wound Care: A Clinical Source Book for HealthCare Professionals, 1990, Chapter 45 (425-430), Health Management Publications, Inc., King of Prussia, PA USA.

* cited by examiner

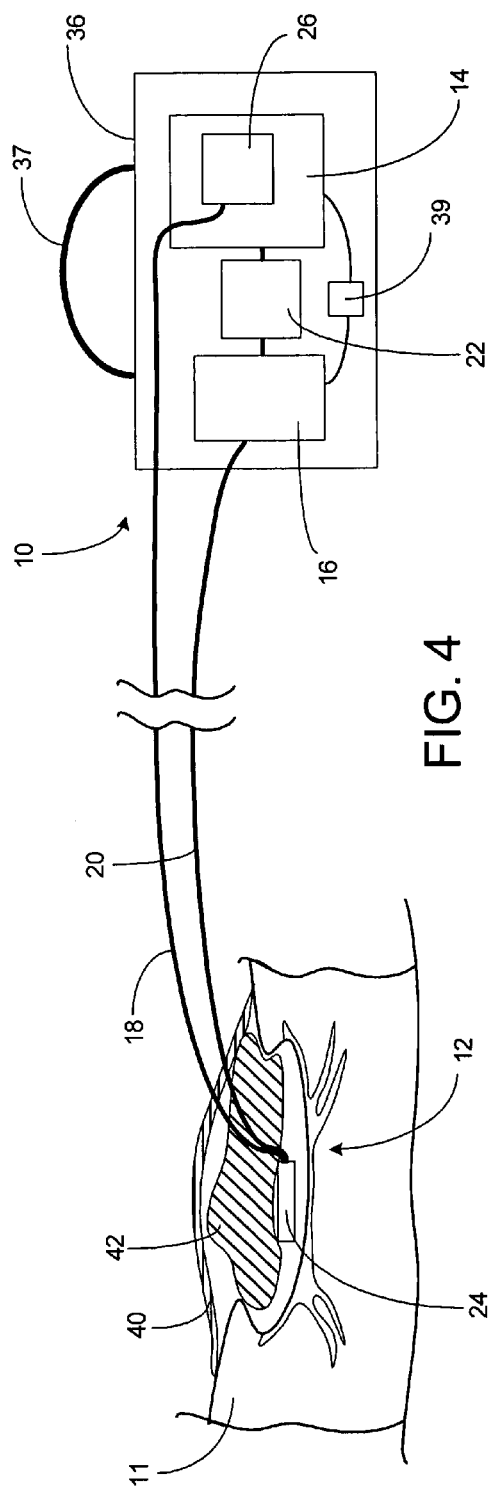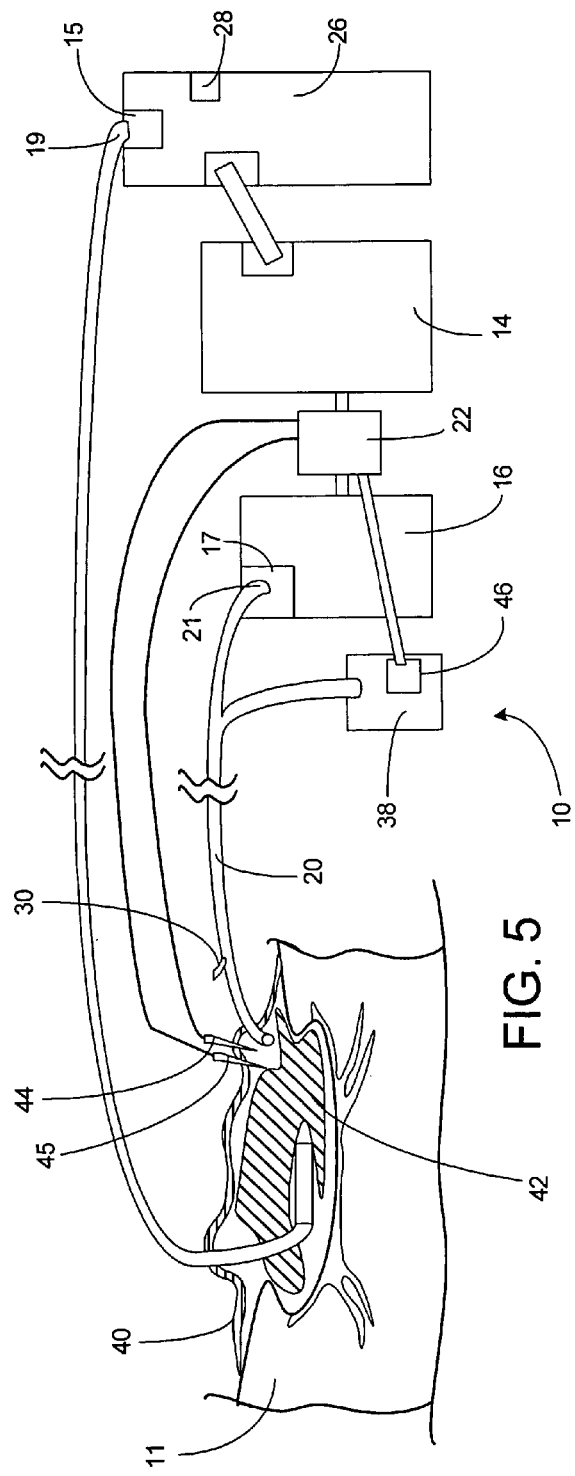

WOUND CARE SYSTEM

CROSS-REFERENCES TO RELATED APPLICATIONS

This application claims priority from co-pending U.S. Provisional Patent Application Ser. No. 60/738,690 filed on Nov. 21, 2005, entitled "Pioneer Hyperbaric Closed Suction Wound Drainage System" which is hereby incorporated by reference.

BACKGROUND OF THE INVENTION

The present invention relates generally to wound care treatment and systems for treating wounds. More specifically, the present invention relates to a system designed for alternating applications of vacuum and hyperbaric wound treatments to a wound site.

The patient care industry is continually searching to provide better services, reduce costs, and improve the equipment used to provide the best possible care to the patients. One such way to advance patient care is to improve the treatment of chronic and acute wounds and various types of therapies to treat these wounds. One of two types of treatments is often used to treat chronic and acute wounds: negative pressure therapy or hyperbaric oxygen therapy.

Negative pressure therapy is the controlled application of sub-atmospheric pressure to a wound using a therapy unit, such as a vacuum or suction device, to expose a wound to negative pressure to help promote wound healing. The wound is typically covered to facilitate this negative pressure and suction at the wound area. Various types of resilient, open cell foam surface dressings are typically sealed within an adhesive drape to provide the sub-atmospheric pressure at the wound site. The exudates drained from the wound site are normally directed to a canister that stores the fluids and/or infectious material until properly disposed. The negative pressure wound therapy has been typically prescribed for chronic and acute wound types such as diabetic wounds, pressure ulcers, abdominal wounds, trauma wounds, various burns, flaps and grafts. One of the limitations of negative pressure therapy is that it may be less effective on patients with vascular disorders, such as diabetes, particularly because negative pressure therapy creates a hypoxic environment at the wound. Current research indicates that wound healing is impaired when the oxygen level is 30 millimeters of mercury (mmHg) or less.

Hyperbaric oxygen therapy is the controlled application of greater-than-atmospheric pressures of oxygen to a wound. Oxygen is typically required for all new cell growth, and chronic or nonhealing wounds tend to exhibit low oxygen tensions, or tend to be ischemic. A wound can become dormant if the amount of wound tissue that is poorly oxygenated reaches a critical mass. In this state, the body may no longer recognize the need to heal that area, which exacerbates the lack of oxygen in that wound and thus substantially prevents healing of the wound by the body. Oxygen therapy is particularly useful for patients with poor circulation. In addition to helping kill bacteria, oxygen applied to an open wound at a hyperbaric level is dissolved into the wound and absorbed by the surface wound tissue. The cells of the wound tissue that absorb the oxygen will begin metabolic activity in response to the increased oxygen tension. Once the oxygen source is removed, the previously active cells request more oxygen from the body. The body responds by beginning to form new blood cells, and thus, starting the healing process.

Typically, hyperbaric oxygen therapy is performed by placing the patient into a hyperbaric chamber that encompasses the full body of the patient or an entire extremity, such as a leg or an arm. Such chambers are problematic due to their lack of portability, the difficulty in sterilization of the chambers between patients, and the potential adverse effects of breathing oxygen at hyperbaric pressure. It would be preferable if the hyperbaric oxygen treatment were localized at the wound rather than applied to the patient's entire body or extremity.

While both negative pressure and hyperbaric oxygen therapies are each believed to be effective when administered as separate wound care treatments, many patients may benefit from a treatment plan incorporating both negative pressure and hyperbaric oxygen therapies. Because existing hyperbaric oxygen treatment is typically performed in a hyperbaric chamber, switching between negative pressure therapy and hyperbaric oxygen therapy is a long process. Before entering a hyperbaric oxygen chamber, a patient would first have to be disconnected from the negative therapy device and the negative pressure therapy dressing—which typically includes packing materials, a drain, tubing, and sealing material—would have to be removed. Then, following hyperbaric oxygen treatment, a new negative pressure dressing would have to be applied. These procedures are wasteful and time-consuming, making it difficult, if not impossible, to alternate between negative pressure therapy and hyperbaric oxygen therapy every few minutes or less.

It would be preferable if an apparatus were capable of localized alternating administration of negative pressure and hyperbaric oxygen therapies to treat a single wound without requiring a change of dressing.

BRIEF SUMMARY OF THE INVENTION

Disclosed is an apparatus for the treatment of a wound on a patient. The apparatus includes a drain line configured for attachment to a negative pressure source and for removing exudate from the wound; a supply line configured for attachment to a fluid source and for supplying fluid to the wound; and a controller. The controller is configured to cause negative pressure therapy to be administered to the wound via the drain line. The controller is further configured to cause hyperbaric fluid therapy to be administered to the wound via the supply line.

The controller is further configured to cause hyperbaric fluid therapy to be administered to the wound at an absolute pressure of at least approximately 1.5 atmospheres via the supply line.

Also disclosed is a wound treatment apparatus that includes a drain line configured for attachment to a negative pressure source and for removing exudate from the wound. The apparatus further includes a supply line configured for attachment to a fluid source and for supplying fluid to the wound and a controller. The controller is configured to cause negative pressure therapy to be administered to the wound for a first time period via the drain line, and cause hyperbaric fluid therapy to be administered to the wound for a second time period via the supply line, wherein the first time period is approximately two to three times as long as the second time period.

Also disclosed is a portable wound treatment apparatus. The portable wound treatment apparatus includes a negative pressure source configured for operative engagement with a wound dressing via a drain line and a fluid source configured for operative engagement with a wound dressing via a supply line. The apparatus also includes a controller that is configured to cause negative pressure therapy to be administered to the wound, and also to cause hyperbaric fluid therapy to be administered to the wound at an absolute pressure of at least approximately 1.5 atmospheres. The apparatus further includes a housing configured to house the negative pressure source, the fluid source and the controller.

Further disclosed is a portable wound treatment apparatus including a negative pressure source configured for operative engagement with a wound dressing via a drain line. The apparatus also includes a fluid source configured for operative engagement with a wound dressing via a supply line, a controller and a housing configured to house the negative pressure source, the fluid source and the controller. The controller is configured to cause negative pressure therapy to be administered for a to the wound first time period, and cause hyperbaric fluid therapy to be administered to the wound for a second time period, wherein the first time period is approximately two to three times as long as the second time period.

Also disclosed is a wound treatment apparatus comprising including a drain line configured for attachment to a negative pressure source and for removing exudate from the wound and a supply line configured for attachment to a fluid source and for supplying fluid to the wound. The apparatus further includes a controller that is configured to cause negative pressure therapy to be administered to the wound via the drain line, and to cause hyperbaric fluid therapy to be administered to the wound at via the supply line. The controller is further configured to control the administration of negative pressure therapy and hyperbaric fluid therapy such that the administration of negative pressure therapy and hyperbaric fluid therapy is cyclical and the hyperbaric fluid therapy is administered to the wound for no more than 30 minutes during each cycle.

Also disclosed is a method for treating a wound. The method includes applying to the wound a dressing that engages a supply line and a drain line; connecting the supply line to a fluid source; connecting the drain line to a negative pressure source; administering negative pressure therapy to the wound via the supply line; and administering hyperbaric fluid therapy to the wound at an absolute pressure of at least 1.5 atmospheres via the supply line.

Further disclosed is another method for treating a wound. The method includes applying to the wound a dressing that engages a supply line and a drain line; connecting the supply line to a fluid source; connecting the drain line to a negative pressure source; administering negative pressure therapy to the wound via the drain line for a first time period; and administering hyperbaric fluid therapy to the wound via the supply line for a second time period. The first time period is approximately two to three times as long as the second time period.

Also disclosed is a method for treating a wound comprising: applying to the wound a dressing that engages a supply line and a drain line; connecting the supply line to a fluid source; connecting the drain line to a negative pressure source; administering negative pressure therapy to the wound via the drain line for a first time period; following the administration of negative pressure therapy, administering hyperbaric fluid therapy to the wound via the supply line for no more than 30 minutes; and following the administration of hyperbaric fluid therapy, administering negative pressure therapy to the wound via the drain line.

The negative pressure therapy and hyperbaric fluid therapy may be administered intermittently.

The fluid source may be configured to supply a constant flow of fluid such that the administration of negative pressure therapy is accomplished by activating the negative pressure source and the administration of hyperbaric fluid therapy is accomplished by deactivating the negative pressure source.

The administration of negative pressure therapy may also be accomplished by activating the negative pressure source and reducing the flow of fluid from the fluid source. Similarly, the administration of hyperbaric fluid therapy may be accomplished by deactivating the negative pressure source and increasing the flow of fluid from the hyperbaric fluid source.

The administration of negative pressure therapy and hyperbaric fluid therapy may also be adjusted in response to information received from a sensor, such as a diffusion sensor, that measures tissue conditions at the wound.

In addition, the disclosed apparatus may also include either mechanical or electronic pressure regulation to ensure that the pressures applied to the wound site do not exceed a desired level.

Also disclosed is a method for preparing a wound dressing. The method includes inserting packing material into the wound; inserting open ends of a supply line and a drain line into the wound; molding a pliable adhesive around the perimeter of the wound such that the adhesive separates the supply line from the skin surrounding the wound and such that the adhesive separates the drain line from the skin surrounding the wound; molding another piece of pliable adhesive over the supply line and the drain line; and placing sealing material over the wound, the packing material, the supply line, the drain line and the adhesive such that the sealing material adheres to both the adhesive and the skin surrounding the adhesive.

It is therefore a general object of the present invention to provide an improved apparatus for the treatment of wounds.

Another object of the present invention is to provide an apparatus that provides both negative pressure therapy and hyperbaric fluid therapy to a wound site.

These and further features of the present invention will be apparent with reference to the following description and attached drawings. In the description and drawings, particular embodiments of the invention have been disclosed in detail as being indicative of some of the ways in which the principles of the invention may be employed, but it is understood that the invention is not limited correspondingly in scope. Rather, the invention includes all changes, modifications and equivalents coming within the spirit and terms of the claims appended hereto.

Features that are described and/or illustrated with respect to one embodiment may be used in the same way or in a similar way in one or more other embodiments and/or in combination with or instead of the features of the other embodiments.

BRIEF DESCRIPTION OF THE SEVERAL VIEWS OF THE DRAWINGS

FIG. 4 is an embodiment of a portable apparatus made in accordance with the current disclosure positioned on a wound;

FIG. 5 is an alternate embodiment of an apparatus made in accordance with the current disclosure positioned on a wound;

DETAILED DESCRIPTION OF THE INVENTION

The invention relates to a novel therapeutic method and apparatus capable of administering both negative pressure therapy and hyperbaric fluid therapy for wound healing. Preferably, negative pressure therapy and hyperbaric fluid therapy, such as hyperbaric oxygen, are intermittently applied to the wound area to remove exudate from the wound and to infuse oxygen into the wound. It is believed that the controlled application of these therapies can greatly increase wound healing success, both clinically and aesthetically, and minimize wound healing time.

The apparatus includes a drain line that attaches to a negative pressure source and is used to remove exudate from the wound. The apparatus also includes a supply line that attaches to a fluid source, such as an oxygen source, and is used to supply fluid to the wound under positive pressure. The system further includes a controller that controls the administration of negative pressure therapy via the drain line and the administration of hyperbaric fluid therapy via the supply line. The apparatus is thus capable of alternating between negative pressure therapy and hyperbaric fluid therapy in an automated manner without requiring clinician assistance and without necessitating a wound dressing change. Moreover, the apparatus can also be made portable because it provides localized therapy without requiring a chamber encompassing a patient's entire body or extremity.

Monitoring of the therapy results, such as monitoring of oxygen levels at the wound site or monitoring of exudate removal, allows the wound treatment therapy to be tailored to each individual to maximize the therapeutic effect while minimizing therapy duration.

Figure 1:
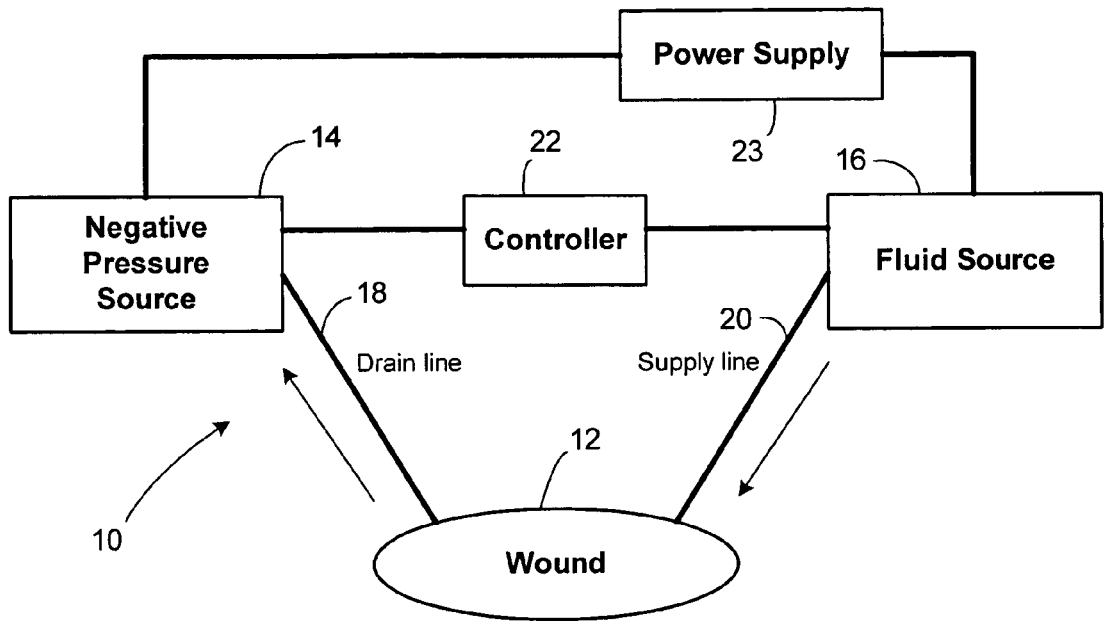
FIG. 1 is a schematic view of an apparatus made in accordance with the current disclosure.

Referring generally now to FIG. 1, a wound treatment apparatus 10 according to the present invention is illustrated schematically. The apparatus 10 includes a drain line 18 that is attached to a negative pressure source 14. The drain line 18 is preferably positioned to remove exudates from the wound 12. The apparatus 10 also includes a supply line 20 that is attached to a fluid source 16. The supply line 20 is preferably positioned to supply fluid to the wound 12. A controller 22 functions to control the therapy administered by the wound treatment apparatus 10 to the wound 12.

As will be understood by those skilled in the art, the controller 22 may be implemented as a control system or even as a control circuit, such as one or more of the following: programmable circuit, integrated circuit, memory and I/O circuits, an application specific integrated circuit, microcontroller, complex programmable logic device, field programmable gate arrays, other programmable circuits, or the like.

The controller 22 can cause the wound treatment apparatus 10 to administer negative pressure therapy to the wound 12 via the drain line 18. The controller 22 can also cause the wound treatment apparatus 10 to administer hyperbaric fluid therapy to wound 12 via the supply line 20. Preferably, hyperbaric fluid therapy is administered to the wound 12 at an absolute pressure of at least approximately 1.5 atmospheres.

In operation, negative pressure therapy and hyperbaric oxygen therapy may each be administered intermittently. In other words, negative pressure therapy and hyperbaric fluid therapy may be administered in alternating treatments where the wound treatment apparatus 10 cycles between negative pressure therapy and hyperbaric fluid therapy or, only one type of treatment (i.e. negative pressure therapy or hyperbaric fluid therapy) may be administered in an intermittent manner such that the wound treatment apparatus 10 cycles between administering treatment to the wound 12 and not administering treatment to the wound 12.

For example, controller 22 may be configured to cause negative pressure therapy to be administered to the wound 12 via the drain line 18 for a first time period and hyperbaric fluid therapy to be administered to the wound 12 via the supply line 20 for a second time period. In one presently preferred embodiment, the first time period during which negative pressure therapy is administered is approximately two to three times as long as the second time period during which hyperbaric fluid therapy is administered. The controller 22 may be further configured to cause hyperbaric fluid therapy to be administered immediately following the cessation of the administration of negative pressure therapy and to cause negative pressure therapy to be administered immediately following the cessation of the administration of hyperbaric fluid therapy.

The administration of negative pressure therapy and hyperbaric fluid therapy may be controlled using a variety of methods. For example, the fluid source 16 may be configured to supply a constant flow of fluid. The controller 22 may be configured to cause the administration of negative pressure therapy by activating the negative pressure source 14, which would create a negative pressure environment at the wound 12 even though the wound 12 would continue to be exposed to fluid from the fluid source 16. The controller 22 may be further configured to cause the administration of hyperbaric fluid therapy by deactivating the negative pressure source 14, thereby causing the wound 12 to be exposed only to the fluid from the fluid source 16 and causing pressures at the wound 12 to build to hyperbaric levels determined by, among other factors, the flow rate of the fluid.

Another mechanism for controlling the administration of negative pressure therapy and hyperbaric fluid therapy is to use the controller 22 to control both the negative pressure source 14 and the fluid source 16. Thus, the controller 22 may be configured to cause the administration of negative pressure therapy by activating the negative pressure source 14 and either reducing the flow from or deactivating the fluid source 16. Similarly, the controller 22 may be further configured to cause the administration of hyperbaric fluid therapy by deactivating the negative pressure source 14 and increasing the flow of fluid from the fluid source 16.

Alternatively, the controller 22 may include two controllers, one for each device. The controller that controls the fluid source 16 may be configured to detect the state of the negative pressure source 14 or the state of the environment surrounding the wound 12. Upon determining an end of a negative pressure therapy cycle, the controller controlling the fluid source 16 could cause the administration of hyperbaric fluid therapy by activating or increasing the fluid flow from the fluid source 16. Conversely, the controller that controls the negative pressure source 14 could be configured to detect the state of the fluid source 16 or the state of the environment surrounding the wound 12. Upon determining an end of a hyperbaric fluid therapy cycle, the controller controlling the negative pressure source 14 could cause the administration of negative pressure therapy by activating the negative pressure source 14.

While each of the negative pressure therapy and the hyperbaric fluid therapy could potentially be administered to the wound 12 for hours before alternating to the other therapy, it is presently preferred that the controller 22 cause negative pressure therapy to be administered to the wound 12 for relatively short periods of time. For example, negative pressure therapy may be administered for approximately 20 seconds to approximately 180 seconds before moving on to hyperbaric fluid therapy or to non-therapy in the event that the apparatus is set to intermittently apply only negative pressure therapy. Similarly, the controller 22 may cause hyperbaric fluid therapy to be administered to the wound 12 for approximately 10 seconds to approximately 60 seconds before moving on to negative pressure therapy or to non-therapy in the event that the apparatus is set to intermittently apply only hyperbaric pressure therapy.

Moreover, the negative pressure therapy and the hyperbaric fluid therapy may be administered in a cyclical manner. For each cycle consisting of negative pressure therapy administration and hyperbaric fluid therapy administration, the administration of hyperbaric fluid therapy may be limited to no more than 30 minutes. In other words, following the administration of negative pressure therapy for a first time period, hyperbaric fluid therapy is administered for no more than 30 minutes, after which the negative pressure therapy is administered again for some time period, which may be the same as the first time period. Hyperbaric fluid therapy would then preferably be administered again for no more than 30 minutes, after which negative pressure therapy would be administered again.

In addition, the controller 22 may also be capable of selectively causing the cessation of negative pressure therapy without causing the cessation of the hyperbaric fluid therapy. Similarly, the controller 22 is preferably configured to be capable of selectively causing the cessation of hyperbaric fluid therapy without causing the cessation of the negative pressure therapy.

As will be understood by those of skill in the art, the administration of negative pressure therapy generally involves exposing the wound 12 to pressures of less than 1 atmosphere. The pressures employed during negative pressure therapy may include absolute pressures ranging from approximately 0 mmHg to approximately 300 mmHg. Preferably, the absolute pressure ranges from approximately 60 mmHg to approximately 160 mmHg during the administration of negative pressure therapy.

As will also be understood by those of skill in the art, the administration of hyperbaric fluid therapy involves exposing the wound 12 to a fluid at greater than atmospheric pressures. Preferably, the wound 12 is subjected to an absolute pressure ranging from approximately 1.5 atmospheres to approximately 3 atmospheres during the administration of hyperbaric fluid therapy.

The negative pressure source 14 can be any suitable suction device such as a vacuum, a manual, mechanical, or electrical pump, a hospital room suction line, or any other device exhibiting vacuum or suction capabilities. The fluid source 16 can be a suitable fluid supply device and preferably is an oxygen source or a humidified oxygen source, such as an oxygen concentrator, oxygen canister, or oxygen supplied from a hospital room oxygen line. For example, the fluid source 16 may administer oxygen or humidified oxygen at approximately 0.1 liters per minute to approximately 3 liters per minute. Preferably, the fluid source 16 administers oxygen or humidified oxygen at approximately 1 liter per minute to approximately 2 liters per minute.

Also, the negative pressure source 14 and the fluid source 16 may be powered by a single power source, such as a wall plug or a rechargeable battery, and may share a power supply, such as power supply 23. Further, the negative pressure source 14 and the fluid source 16 may both reside in a single portable casing that houses the negative pressure source 14 and the fluid source 16 as one unit.

The drain line 18 may be surgical tubing, oxygen tubing or any other suitable type of line for removing exudate from a wound site. The supply line 20 may be surgical tubing, oxygen tubing or any other suitable type of line for carrying fluid, such as oxygen, to a wound site. In addition, part of the drain line 18 and part of the supply line 20 may be formed by a multi-lumen tube.

Figure 2:
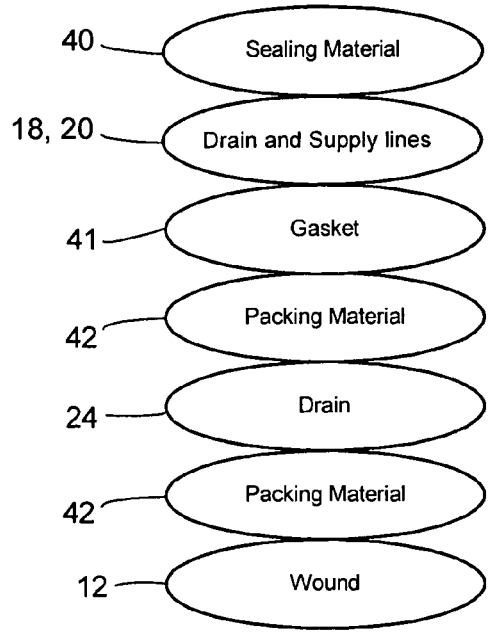
FIG. 2 is a schematic illustration of an example wound dressing and surrounding elements made in accordance with the current disclosure.

To perform localized administration of negative pressure therapy and hyperbaric fluid therapy, the drain line 18 and supply line 20 preferably engage a wound dressing. FIG. 2 is a schematic illustration of an example wound dressing and surrounding elements made in accordance with the current disclosure. As shown in FIG. 2, the dressing includes packing material 42 above the wound 12 and a drain 24 atop the packing material 42. The packing material may be, for example, gauze, foam dressing/packing, sponges, or the like. Preferably, the packing material is anti-microbial gauze saturated with saline.

Figure 6:
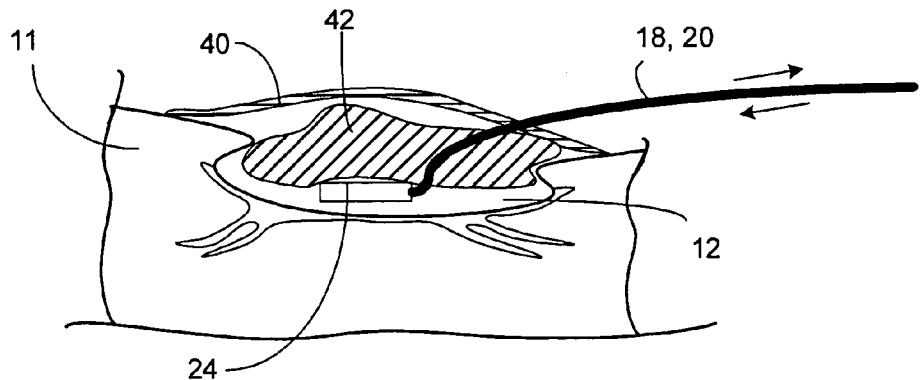
FIG. 6 is a side view of a wound being treated by an apparatus made in accordance with the current disclosure and using an embodiment of a drain made in accordance with the current disclosure.
Figure 7:
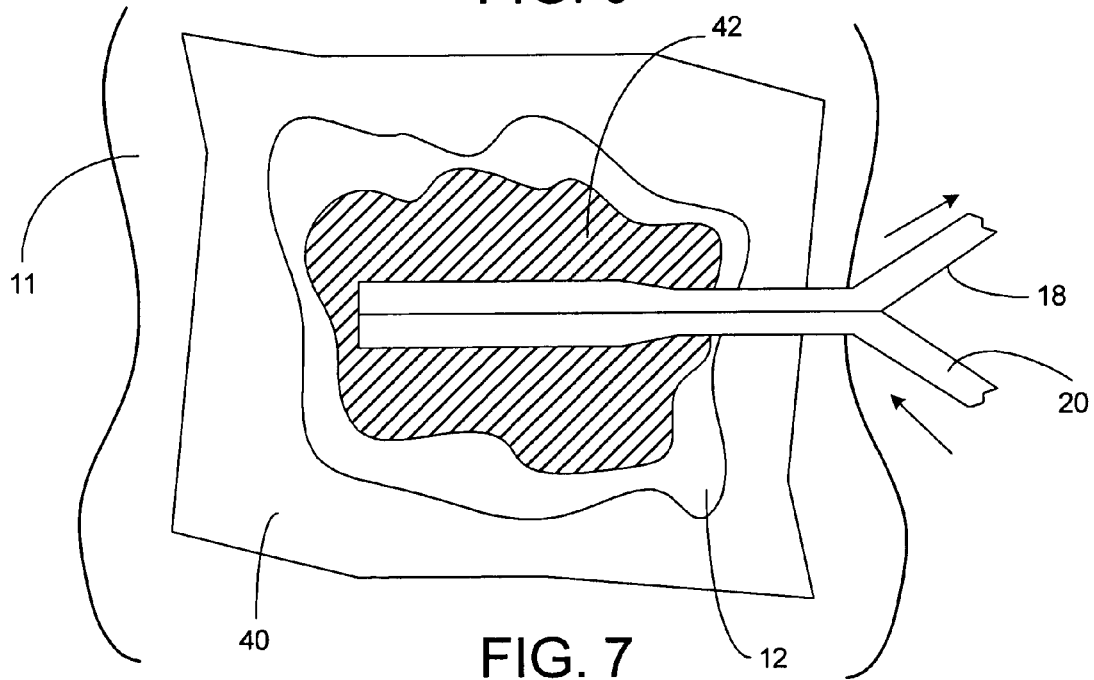
FIG. 7 is top view of a wound being treated using the drain of FIG. 6.
Figure 8:
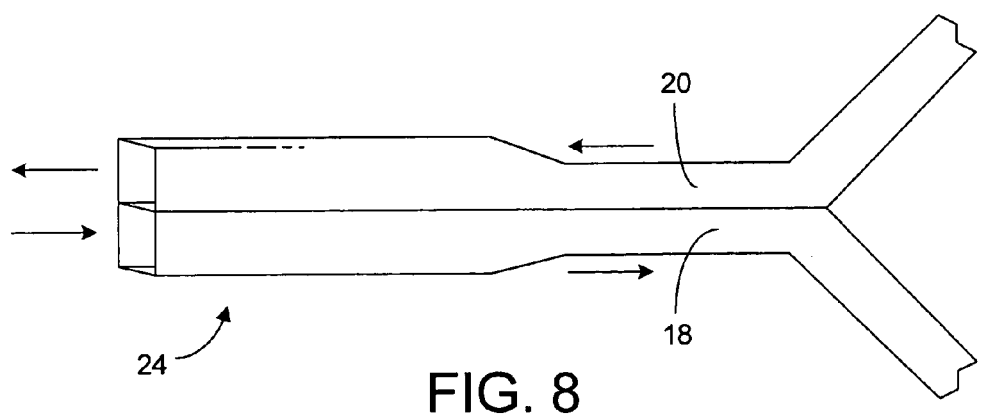
FIG. 8 is a view of the drain of FIGS. 6 and 7.

The drain device 24 may be included as part of the drain line 18 or attached to the end of the drain line 18 opposite the negative pressure source 14. Suitable drain devices include Jackson-Pratt silicon drain, flat drain, round channel drain, fluted drain, drain tube, Kremlin drain, or other drains capable of removing exudates from within or on top of the wound 12. An example of a drain 24 is illustrated in FIGS. 6-8.

Atop the drain 24 is more packing material 42. The dressing further has a gasket 41 made from pliable adhesive material molded around the surrounding edge of the wound 12. The drain line 18 and the supply line 20 are atop the gasket 41. Optionally, additional gasket 41 material is included atop the drain line 18 and supply line 20 for engaging the drain line 18 and the supply line 20. The gasket 41 material may be, for example, an Eakin Cohesive Seal.

Sealing material 40 surrounds the wound 12, the drain 24, the packing material 42 and the gasket 41. The sealing material 40 can adhere to the gasket 41 and the skin surrounding the wound 12. Preferably, the dressing is capable of maintaining adherence during administration of hyperbaric fluid therapy at pressures of at least 3 atmospheres. The sealing material 40 preferably has adhesive properties to withstand the pressure induced by the supply of hyperbaric fluid from the fluid source 16 and the negative pressures drawn by the negative pressure source 14.

It will be understood by those skilled in the art that various types of dressings may be used. For example, the drain 24 may be positioned above the packing material 42 or below the packing material 42, as opposed to sandwiched between packing material 42 as shown. Also, the drain 42 and sealing material 40 may be incorporated as one device. In addition, the dressing may also include a protective mesh separating the packing material 42 from the wound 12.

Figure 3:
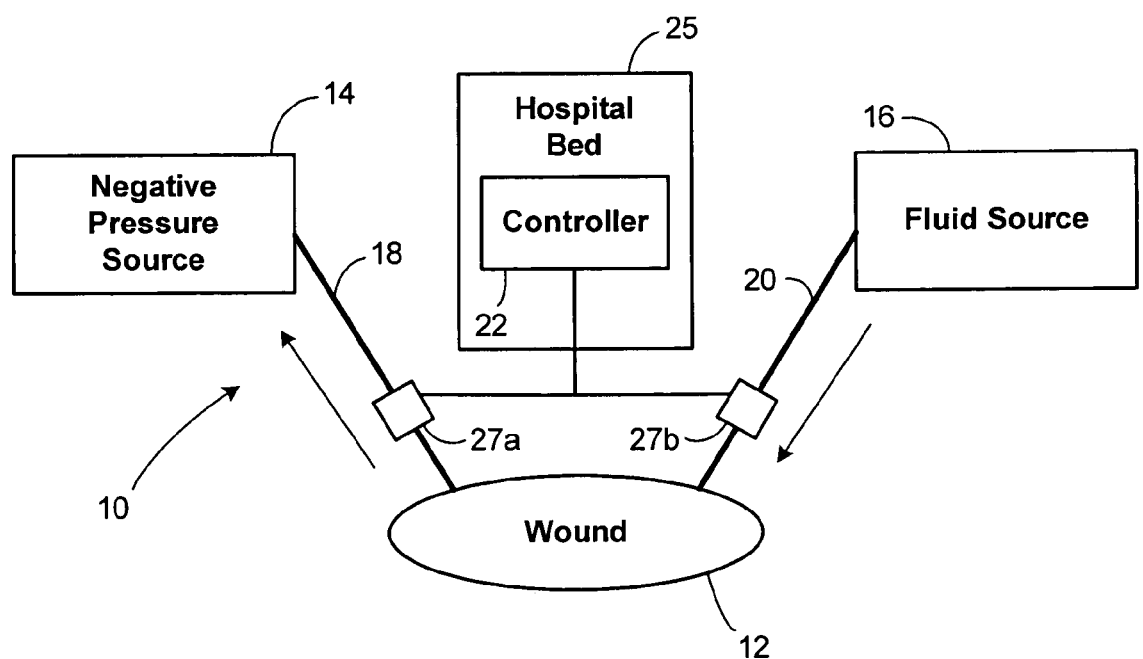
FIG. 3 is a schematic illustration of a hospital bed embodiment of apparatus made in accordance with the current disclosure.

Turning next to FIG. 3, a schematic illustration of a hospital bed embodiment of apparatus made in accordance with the current disclosure is provided. Because of the presence of both a negative pressure supply 14 and a fluid supply 16 in many hospital rooms, it may be desirable to incorporate the controller 22 into a hospital bed 25, which may include the bed frame and/or the mattress. Thus, the controller 22 in a hospital bed 25 is preferably used to administer negative pressure therapy and hyperbaric pressure therapy on a wound 12 using a hospital room suction line as the negative pressure source 14 and the hospital room oxygen line as the fluid source 16. To control the pressures at the wound, the apparatus further includes valves 27*a* and 27*b* that are and located on the drain line 18 and supply line 20 and controlled in an automated manner by the controller 22. The apparatus may further include sensors to provide the controller 22 with information used by the controller 22 in controlling the valves 27 and 27*b*.

Turning next to FIG. 4, a portable wound treatment apparatus 10 made in accordance with the current disclosure and positioned on a wound 12 is illustrated schematically. Like FIGS. 1 and 3, FIG. 4 includes a negative pressure source 14, a fluid source 16, a controller 22, drain line 18 and supply line 20. Attached to the drain line 18 is a drain 24 placed in the wound 12. A dressing including packing material 42 and a sealing material 40 is placed over the wound 12 and adhered to the skin 11.

To make the apparatus of FIG. 3 portable, the negative pressure source 14, the controller 22 and the fluid source 16 are positioned in a housing 36 to house the negative pressure source 14 and the fluid source 16 as a single unit. The housing 36 may also house the collection device 26 and a humidification device, such as the humidification device 38 of FIG. 5. The humidification device 38 may be connected to the supply line 20 to add moisture to fluid being supplied to the wound 12. In addition, it may be desirable to include a power source 39, such as a rechargeable battery, within the housing 36. The power source 39 may run both negative pressure source 14 and the fluid source 16. The casing 36 may further include a handle 37 used to transport the apparatus 10 and/or suspend the apparatus 10 on a medical support such as an IV stand.

The drain 24, in conjunction with the drain line 18 under operation of the negative pressure source 14, may operate to transport exudates from the wound 12 to a collection device 26 connected to the drain line 18. The exudates can be stored in the collection device 26 until properly disposed of.

Turning next to FIG. 5, another embodiment of a wound treatment apparatus 10 made in accordance with the current disclosure and positioned on a wound is illustrated schematically. Like FIGS. 1, 3 and 4, FIG. 5 includes a negative pressure source 14, a fluid source 16, a controller 22, a drain line 18 and a supply line 20. Attached to the drain line 18 is a drain 24 placed in the wound 12. A dressing including packing material 42 and a sealing material 40 is placed over the wound 12 and adhered to the skin 11. Following placement, the sealing material 40 may create a fluidic chamber around the wound 12.

The apparatus of FIG. 5 also includes a collection device 26 connected to the drain line 18 for storing exudates from the wound 12 until properly disposed of. As shown, the drain line 18 includes a drain line connection end 19 and the collection device 26 includes a drain line portal 15 shaped to accept the drain line connection end 19. Preferably, the drain line portal 15 is shaped to accept only the drain line connection end 19 so as to avoid unintentionally connecting the supply line 20 to the drain collection device 26. The collection device 26 may also include a collection device sensor 28 engaging the collection device 26 and connected to the controller 22 to indicate the level to which the collection device 26 is filled with exudates. The controller 22 may be configured to stop the administration of negative pressure therapy upon receiving information from the collection device sensor indicating that the collection device is full. In one embodiment, the collection device sensor 28 may notify the controller 22 and a warning can be issued to the user and/or the apparatus 10 can be shut down.

The supply line 20 supplies fluid to the wound site. Preferably, fluid supply 16 has a supply line portal 17 that is shaped to accept only a supply line connection end 21 so as to avoid unintentionally connecting the drain line 18 to the fluid source 16. The wound treatment apparatus 10 may also include a pressure regulator to help prevent excessive pressurization of the wound site. The pressure regulator may be, for example, a pressure sensor 44, which can be positioned to determine the pressure at the wound site. For example, the pressure sensor 44 may be positioned at the wound site or anywhere along the pathway between the fluid source 16 and the wound 12 or anywhere along the pathway between the negative pressure source 14 and the wound 12. The pressure sensor 44 may be any type of device capable of providing information to either a user or the controller 22 about the pressure at the wound site. The pressure sensor 44 may be operatively connected to the controller 22 and the controller 22 may be configured to adjust the negative pressure therapy or the hyperbaric fluid therapy in response to information received from the pressure sensor 44.

The pressure regulator may also be a mechanical pressure regulator 30 positioned along the supply line 20 between the wound 12 and fluid supply 16. The mechanical pressure regulator 30 may be used in conjunction with the pressure sensor 44. The mechanical pressure regulator 30 is preferably configured to actuate when the pressure in the supply line 20 at the pressure regulator 30 exceeds a set threshold. The actuation of the mechanical pressure regulator 30 causes a reduction of the supply line 20 pressure. For example, the mechanical pressure regulator 30 may include a release valve that opens when the pressure within the supply line 20 exceeds a certain threshold.

Figure 9:
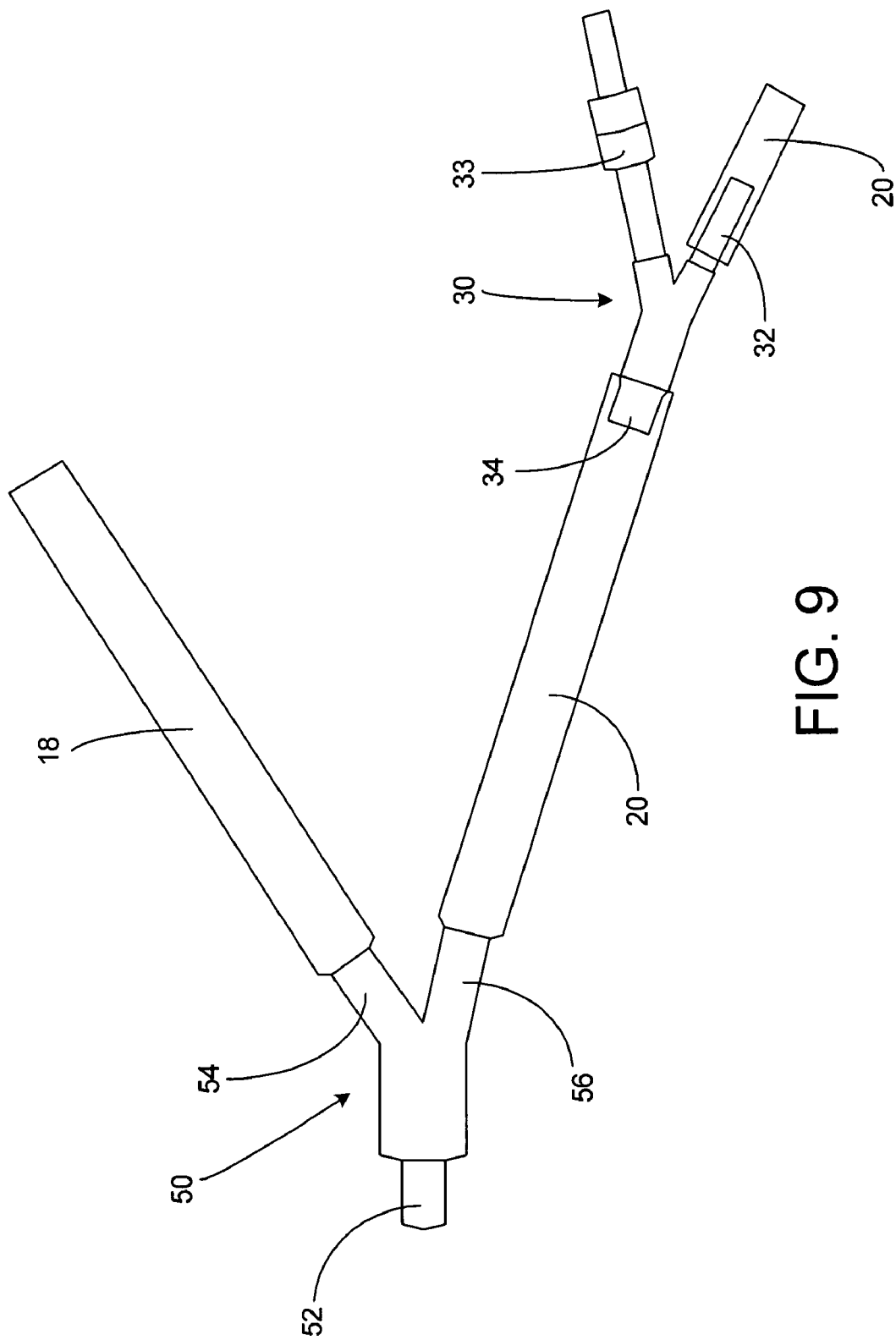
FIG. 9 is an embodiment of the supply and drain lines made in accordance with the current disclosure.

One embodiment of the mechanical pressure regulator 30 is illustrated in FIG. 9. As shown, the mechanical pressure regulator 30 is a Y valve. One side of the Y valve has a wound connection line 34 that is operatively connected to the wound 12. The opposite side of the Y valve has two pathways. One of the pathways has a release valve 33 for venting excess fluid. The other pathway has a fluid source connection line 32 for connecting the mechanical pressure regulator 30 to the fluid source 16. The mechanical pressure regulator 30 is preferably configured to actuate when the pressure at the mechanical pressure regulator 30 exceeds a set threshold. Actuation of the mechanical pressure regulator 30 causes the release valve 33 to open. The set threshold may be determined by the desired pressure to be applied to the wound 12 during hyperbaric fluid therapy. The actuation of the mechanical pressure regulator 30 then causes a reduction of the supply line 20 pressure as fluid is vented out of the system.

In addition, the mechanical pressure regulator 30 may be configured to maintain a reduced pressure within the supply line 20 following the actuation of the mechanical pressure regulator 30. While the venting of fluid may cause a reduction in the supply line 20 pressure, the system may equalize if the flow rate of the fluid through the supply line 20 remains constant and the release valve 33 remains open. Thus, the mechanical pressure regulator 30 causes the pressure in the supply line 20 to be maintained at a reduced level.

Also as shown in FIG. 9, the Y valve 50 may connect the drain line 18 and the supply line 20 into a single-lumen tube for engaging the dressing. The Y valve 50 includes a drain connection line 54 and supply connection line 56. The supply line 20 and drain line 18 are merged together by the Y valve 50 and the merged supply line 20 and drain line 18 are engageable with the wound 12 via the wound connection 52.

Also as shown in FIG. 5, the wound treatment apparatus may also include humidification device 38 operatively connected the supply line 20. The humidification device 38 may be configured to humidify the fluid from the fluid source 16 before the fluid is administered to the wound 12. For example, when the fluid source 16 supplies oxygen, the humidification device 38 may function to humidify the oxygen so that humidified oxygen is supplied to the wound 12. In addition, the humidification device 38 may be configured to heat the fluid in the supply line 20, thereby causing an increase in the temperature at the wound 12. Accordingly, the humidification device 38 may comprise a heating element 46 that is operatively connected to the controller 22. Alternatively, a heating element 46 may be a component of the apparatus 10 that is separate from the humidification device 38. In operation, the controller 22 may be configured to cause the heating element 46 to maintain a temperature at the wound 12 above approximately 98 degrees Fahrenheit and below the combustion temperature of the fluid administered during hyperbaric fluid therapy. Also, the heating element 46 may be configured to control the temperature at the wound independent of the controller 22.

The humidification device 38 may also act as a drug delivery device. For example, the humidification device 38 may function to introduce at least one non-oxygen drug into the supply line 20. The non-oxygen drug may be introduced into the humidification device 38 in powder form and may be supplied by the humidification device 38 to the supply line 20 in powder form via gas. The non-oxygen drug may also be supplied in vapor form via humidified gas. Alternatively, a separate drug delivery device may be attached to the supply line 20 to deliver non-oxygen drugs to the wound 12.

Also as shown in FIG. 5, the wound treatment apparatus may further include a diffusion sensor 45 to measure diffusion of fluid, such as oxygen, into the wound 12. The diffusion sensor 45 may be, for example, a transcutaneous oxygen sensor. The diffusion sensor 45 is preferably operably connected to the controller 22 and the controller 22 is preferably configured to adjust at least one of the negative pressure therapy or the hyperbaric fluid therapy in response to information received from the diffusion sensor 45. For example, in response to information received from the diffusion sensor 45 indicating that the fluid diffusion rate is below a desired level, the controller 22 may be configured to cause an increase in at least one of the fluid flow rate or the pressure at the wound 12 during hyperbaric fluid therapy.

The controller 22 may also or alternatively be configured to cause an increase in the duration of the administration of hyperbaric fluid therapy relative to the negative pressure therapy in response to information received from the diffusion sensor 45. Similarly, the controller 22 may be configured to cause a decrease in the duration of the administration of negative pressure therapy relative to the hyperbaric fluid therapy in response to information received from the diffusion sensor 45 indicating that the fluid diffusion rate is below a desired level.

In another embodiment the supply line 20 has a supply line connection end 21 while the fluid source 16 includes a supply line portal 17. The supply line portal 17 is shaped to accept the supply line connection end 21. The drain line 18 includes a drain line connection end 19 while the collection device 26 includes a drain line portal 15 shaped to accept the drain line connection end 19. The supply line portal 17 is shaped such that it will only accept the supply line connection end 21 while the drain line portal 15 is shaped to only accept the drain line connection end 19. This configuration assists in the safe connection of the negative pressure source 14 and fluid source 16 to the proper lines 18 and 20.

The apparatus 10 can include various disposable elements and still maintain the inventive nature disclosed herein. For example, the drain line 18 and supply line 20 as well as the collection device 26, or the container that collects the exudants, the sealing material 40, packing material 42 and other elements that are in or near the wound 12 can be made to be disposable and discarded between uses of the remainder of the apparatus 10 to facilitate sterilization and reduce the potential contamination of subsequent patients by infectious diseases.

Assembly of the apparatus 10 and engagement of the apparatus 10 to a wound 12 can be accomplished as follows. The packing material 42 can be positioned in and around the wound to take up empty space thereby. A drain device 24 can be positioned in and around the wound 12 and connected to the drain line 18. The drain line connection end 19 can be attached to the negative pressure source 14 in the drain line portal 15. The drain line 18 can alternately go through a separate collection device 26 that will collect the exudates from the wound 12. The supply line 20 can also be positioned in or near the wound 12 while the supply line connection end 21 can be inserted into the supply line portal 17 of the fluid source 16. Alternatively the supply line 20 can be connected to a humidification device 38 that will add moisture to the oxygen as it flows to the wound 12.

Figure 10B:
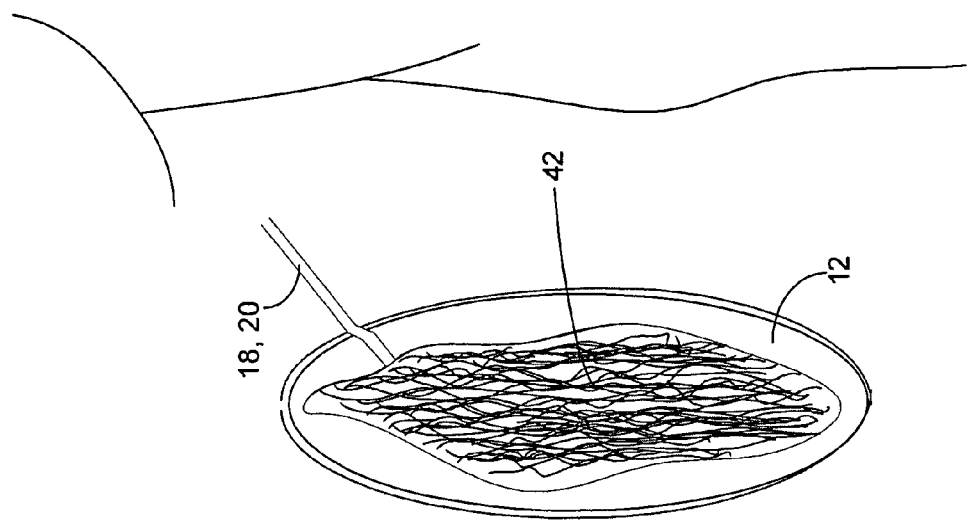
FIGS. 10A-F illustrate the preparation of a wound dressing made in accordance with the current disclosure.
Figure 10A:
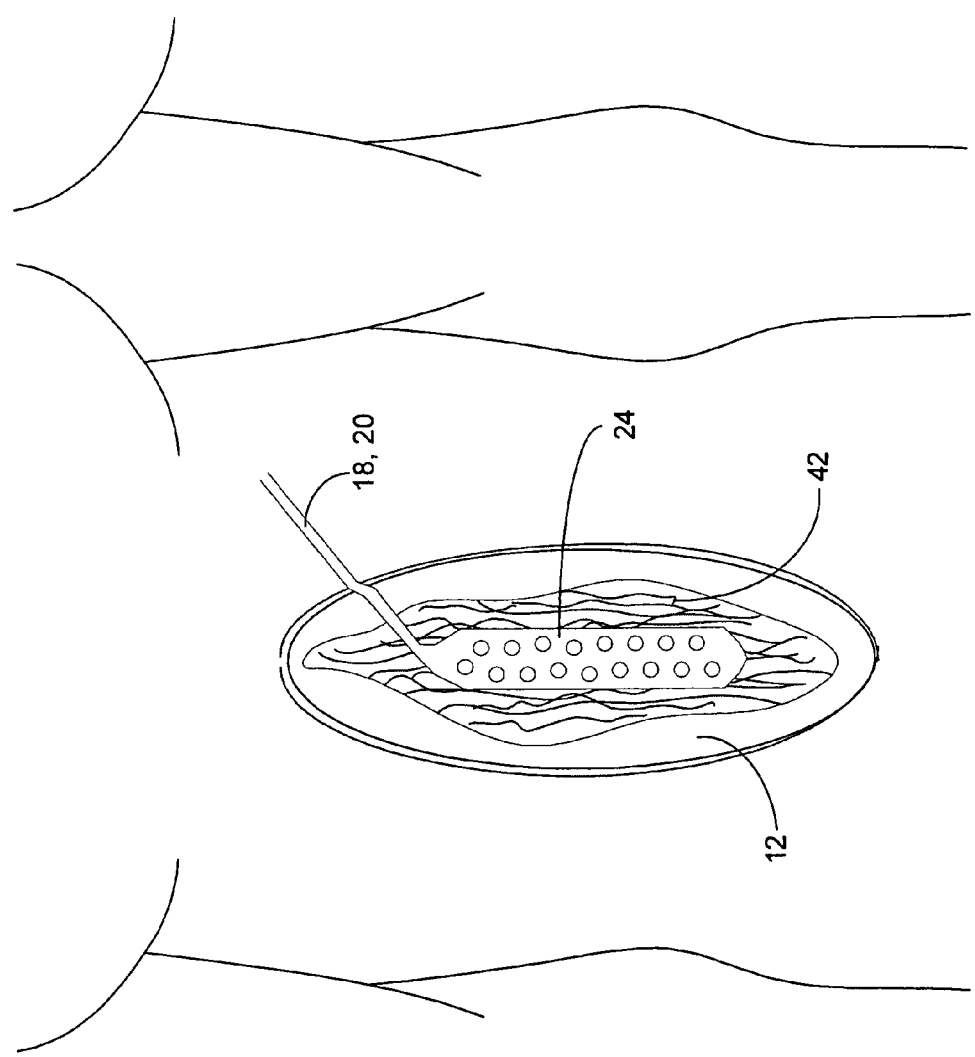

Turning next to FIGS. 10A-F and 11, the preparation of one embodiment of a wound dressing made in accordance with the current disclosure is illustrated schematically and in flow chart form. As shown in FIG. 10A and process block 1102, packing material 42 is inserted into the wound 12. The packing material 42 preferably comprises anti-microbial gauze saturated with saline. Prior to inserting the packing material 42, it may be desirable to insert a protective mesh into the wound 12. Open ends of the supply line 20 and drain line 18 are then inserted into the wound 12 atop the packing material 42. This is illustrated in FIG. 10A and process block 1104. As shown, the process of inserting open ends of the supply line 20 and drain line 18 may involve inserting into the wound 12 a drain 24 connected to the supply line 20 and drain line 18. A multi-lumen tube may form the supply line 20 and the drain line 18. Preferably, additional packing material 42 is inserted atop the drain 24 as shown in FIG. 10B. An example of a drain 24 is illustrated in FIGS. 6-8.

Figure 10D:
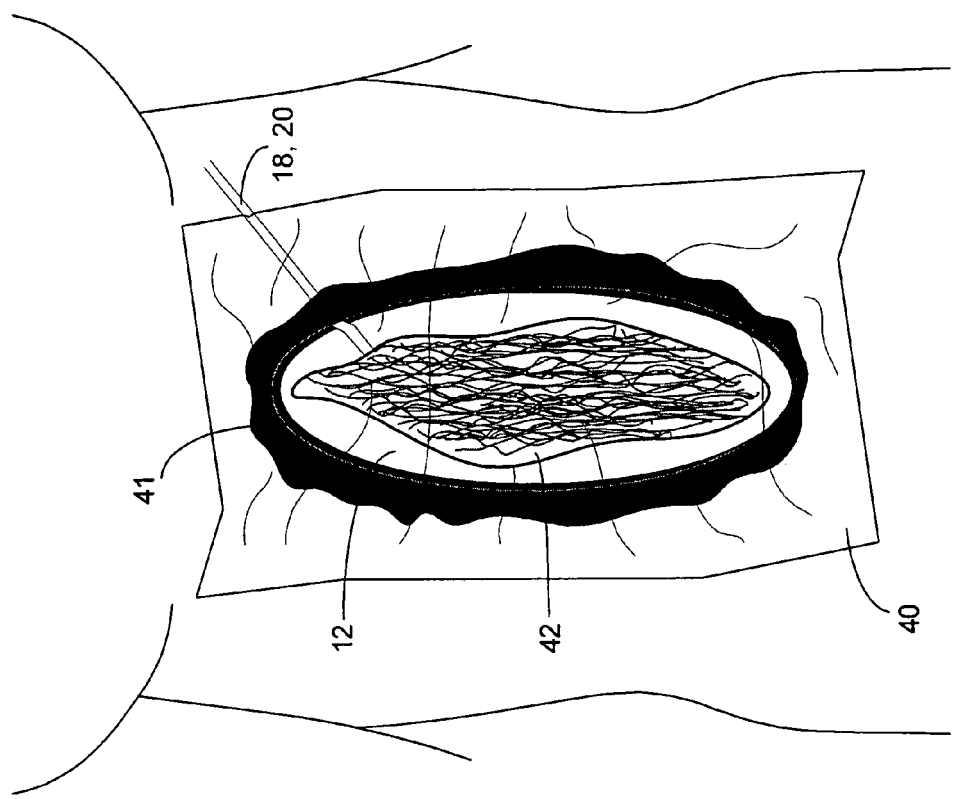
Figure 10C:
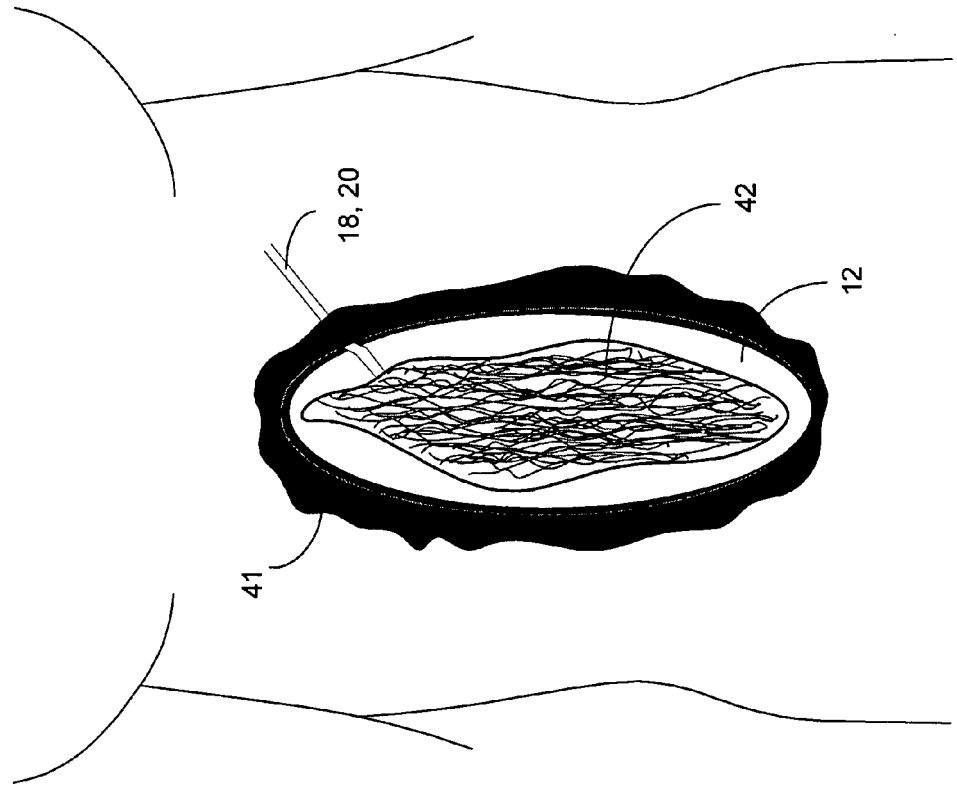

As shown in FIG. 10C and process block 1106, a pliable adhesive gasket 41 is molded around the perimeter of the wound 12. Preferably, the gasket 41 separates supply line 20 and drain line 18 from the patient's skin surrounding the wound 12. The supply line 20 and the drain line 18 are thus engaged with adhesive gasket 41. Preferably, as shown in FIG. 10C and process block 1108, another piece of a pliable adhesive gasket 41 is then molded over the supply line 20 and the drain line 18 to strengthen the engagement. The pliable adhesive gasket 41 may be made from a cohesive seal.

Figure 10E:
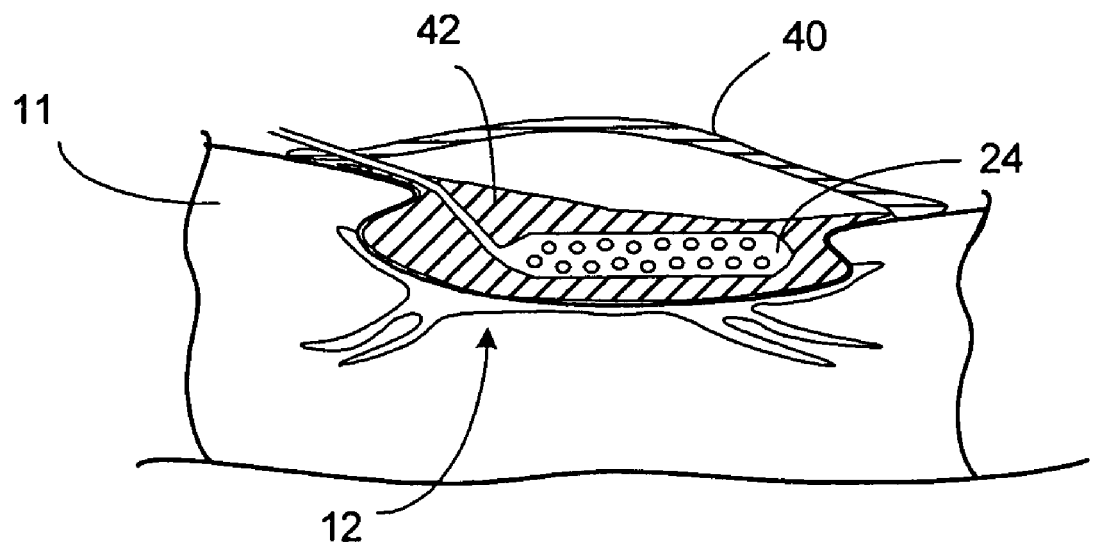
Figure 10F:
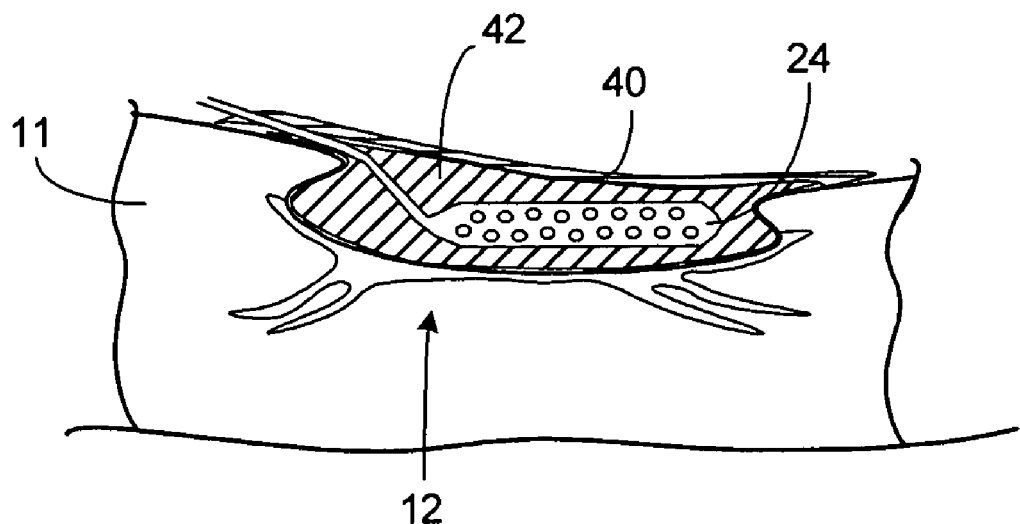
Figure 11:
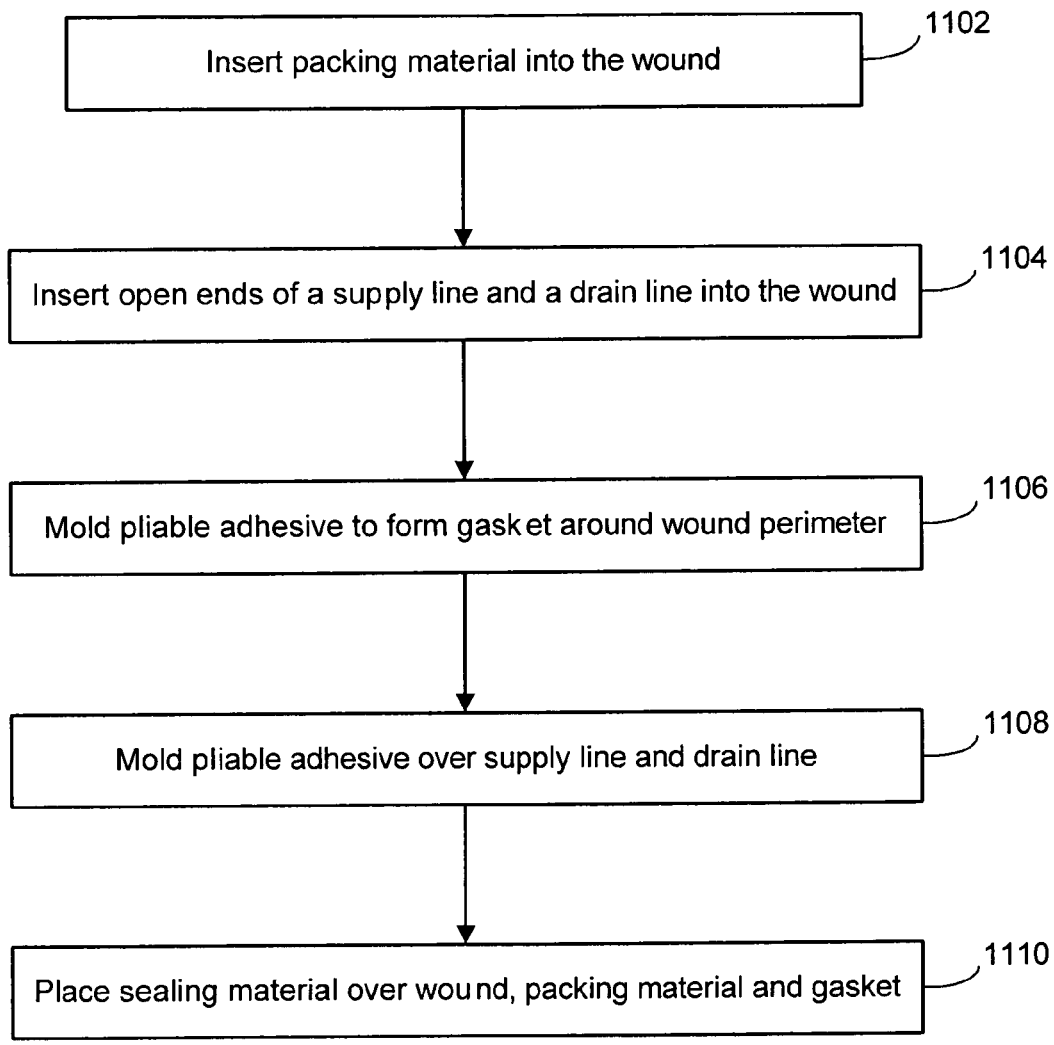
FIG. 11 is a flow chart illustrating a method performed in accordance with the current disclosure.

As shown in FIG. 10D and process block 1110, sealing material 40 is then placed over the wound 12, the packing material 42, the supply line 20, the drain line 18 and the adhesive gasket 41 such that the sealing material 40 adheres to both the adhesive gasket 41 and the skin surrounding the adhesive. FIGS. 10E and 10F show the dressing during hyperbaric pressure therapy and negative pressure therapy, respectively.

Although the invention has been shown and described with respect to certain embodiments, it is obvious that equivalents and modifications will occur to others skilled in the art upon the reading and understanding of the specification. The present invention includes all such equivalents and modifications, and is limited only by the scope of the following claims.

What is claimed is:

1. A wound treatment apparatus comprising:
    a drain line configured for attachment to a negative pressure source and for removing exudate from the wound;
    a supply line configured for attachment to a fluid source and for supplying fluid to the wound;
    a controller configured to:
        cause negative pressure therapy to be administered to the wound via the drain line, and
        cause hyperbaric fluid therapy to be administered to the wound via the supply line for approximately 10 seconds to approximately 60 seconds; and
    a dressing to cover the wound and engage the supply line and the drain line, wherein the dressing comprises a pliable adhesive material molded onto the patient's skin around the perimeter of the wound to form a gasket between the patient's skin and a sealing material opposite the skin.

2. The wound treatment apparatus of claim 1, wherein the pliable adhesive material is molded around and engages the supply line and the drain line.

3. A wound treatment apparatus comprising:
    a drain line configured for attachment to a negative pressure source and for removing exudate from the wound;
    a supply line configured for attachment to a fluid source and for supplying fluid to the wound;
    a controller configured to:
        cause negative pressure therapy to be administered to the wound via the drain line, and
        cause hyperbaric fluid therapy to be administered to the wound via the supply line for approximately 10 seconds to approximately 60 seconds; and
    a dressing to cover the wound and engage the supply line and the drain line, wherein the dressing comprises a sealing material covering the wound.

4. A method for preparing a wound dressing comprising:
    inserting packing material into the wound;
    inserting open ends of a supply line and a drain line into the wound;
    molding a pliable adhesive around the perimeter of the wound such that the adhesive separates the supply line from the skin surrounding the wound and such that the adhesive separates the drain line from the skin surrounding the wound;
    molding another piece of pliable adhesive over the supply line and the drain line; and
    placing sealing material over the wound, the packing material, the supply line, the drain line and the adhesive such that the sealing material adheres to both the adhesive and the skin surrounding the adhesive.

5. The method of claim 4, further comprising inserting a protective mesh prior to inserting the packing material.

6. The method of claim 4, wherein the packing material comprises anti-microbial gauze saturated with saline.

7. The method of claim 4, wherein a multi-lumen tube forms the supply line and the drain line.

8. The method of claim 4, wherein inserting packing into the wound comprises inserting packing below and above the supply line and the drain line.

9. The method of claim 4, wherein inserting open ends of a supply line and a drain line into the wound comprises inserting into the wound a drain connected to the supply and drain line.

10. The method of claim 4, wherein the pliable adhesive is a cohesive seal.

* * * * *